(12) United States Patent
Sannino et al.

(10) Patent No.: US 6,630,422 B1
(45) Date of Patent: Oct. 7, 2003

(54) ABSORBENT POLYMER MATERIAL BASED ON RENEWABLE STARTING MATERIALS

(75) Inventors: Alessandro Sannino, Naples (IT); Giuseppe Mensitieri, Naples (IT); Fausto Esposito, deceased, late of Naples (IT), by Dario Esposito, heir; Matteo Del Nobile, Naples (IT)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 09/445,697

(22) PCT Filed: Jun. 23, 1998

(86) PCT No.: PCT/SE98/01211

§ 371 (c)(1),
(2), (4) Date: Nov. 29, 2000

(87) PCT Pub. No.: WO98/58688

PCT Pub. Date: Dec. 30, 1998

(30) Foreign Application Priority Data

Jun. 24, 1997 (WO) .............................. PCT/SE97/01126

(51) Int. Cl.⁷ .............................. B01J 20/22; C08J 3/07
(52) U.S. Cl. ..................................... 502/402; 521/59
(58) Field of Search ..................... 502/404, 401, 502/159, 402; 527/311, 313, 314, 310; 521/59, 63; 536/80

(56) References Cited

U.S. PATENT DOCUMENTS

| | | | | | |
|---|---|---|---|---|---|
| 4,375,535 | A | * | 3/1983 | Kightlinger et al. | 527/313 |
| 4,952,550 | A | * | 8/1990 | Wallach et al. | 252/194 |
| 4,959,341 | A | * | 9/1990 | Wallach et al. | 134/40 |
| 5,155,194 | A | * | 10/1992 | Kossmehl et al. | 526/238.23 |
| 5,532,350 | A | * | 7/1996 | Cottrell et al. | 536/76 |
| 5,573,994 | A | * | 11/1996 | Kabra et al. | 264/DIG. 16 |
| 5,801,116 | A | * | 9/1998 | Cottrell et al. | 502/401 |
| 6,027,795 | A | * | 2/2000 | Kabra et al. | 438/623 |
| 6,107,432 | A | * | 8/2000 | Engelhardt et al. | 527/311 |
| 6,383,609 | B1 | * | 5/2002 | Annergren et al. | 428/178 |
| 2002/0103160 | A1 | * | 8/2002 | Yoshii et al. | 201/24 |

FOREIGN PATENT DOCUMENTS

WO   WO 95/31500   11/1995

* cited by examiner

*Primary Examiner*—Steven Bos
*Assistant Examiner*—Anthony Kuhar
(74) *Attorney, Agent, or Firm*—Burns Doane Swecker & Mathis LLP

(57) ABSTRACT

A method of production of a highly absorbent, polysaccharide-based material, wherein an aqueous solution containing a starting material including a cross-linkable polysaccharide-based polymer blend of an electrically charged polysaccharide-based polymer and an electrically uncharged polysaccharide-based polymer is subjected to cross-linking in order to obtain a water-swelled gel. The cross-linked, water-swelled gel is dessicated with a polar solvent.

11 Claims, 14 Drawing Sheets

ABSORBENT POLYMER MATERIAL BASED ON RENEWABLE STARTING MATERIALS

TECHNICAL FIELD

The invention pertains to a method for manufacturing of a highly absorbent, polysaccharide based absorption material, wherein a water-containing solution comprising a starting material in the form of a crosslinkable polysaccharide based polymer is subjected to crosslinking in order to obtain a water-swelled gel.

BACKGROUND OF THE INVENTION

For many applications, such as in absorbent articles intended for absorption of body fluids, it has become increasingly more common to use what is known as superabsorbent materials. Superabsorbent materials are polymers which are capable of absorbing liquid in amounts corresponding to several times of the weight of the polymer and which upon absorption form a water-containing gel.

The main advantage of using superabsorbent materials in absorbent articles is that the volume of the absorbent articles can be considerably reduced when compared to the volume of absorbent articles mainly formed from absorbent fibrous materials such as fluffed cellulose pulp, or the like. Another advantage is that superabsorbents, when compared to fibrous absorbents such as, for instance, fluffed cellulose pulp, have a higher capability of retaining liquid under pressure. Such a property is, for instance, advantageous when the absorption material is used in diapers, incontinence guards or sanitary napkins, since absorbed body fluid is retained in the absorbent article and is not squeezed out of the article, for instance when the user is sitting.

However, a disadvantage with many of the superabsorbent materials presently being used in absorbent articles such as diapers, incontinence protectors or sanitary napkins, is that they are not produced from renewable raw materials. In order to solve this problem, it has been suggested that superabsorbents based on different types of renewable starting materials, such as polysaccharides and, in particular, starch, be used. Unfortunately, the polysaccharide-based superabsorbents which have so far been produced exhibit considerably lower absorption capacity than the commonly used polyacry-late-based superabsorbents. Further, the ability of the polysaccharide-based superabsorbents to retain absorbed liquid when the superabsorbent is subjected to load is low in comparison with polyacrylate-based superabsorbents.

In WO 95/31500 a method for producing absorbent, preferably superabsorbent, foam materials by phase separation and crosslinking of a polymer solution is described. The absorbent materials thus obtained exist in the form of a crosslinked open-celled polymer foam, which implies that fluid may pass between cells. By means of the described production method, it is also said to be possible to obtain biodegradeable absorbent foam materials. Preferred polymers for producing the absorbent materials which are disclosed in WO 95/31500 are hydroxyethyl cellulose (HEC) and hydroxypropyl cellulose (HPC), which are preferably crosslinked with divinyl sulphone (DVS).

The known absorbent foam materials are relatively expensive to produce and are primarily intended for medical applications, such as controlled release systems or as artificial skin and blood vessels. However, a further possible use for the described foam materials is said to be in reusable diapers or the like. The high production cost does, however, mean that the known foam materials would, in practice, not be contemplated as absorption material for absorbent articles intended for single use only.

For these reasons, there exists a demand for an improved superabsorbent material based on renewable raw materials. Accordingly, the absorption capacity for polysaccharide-based superabsorbents needs to be improved in order to make such superabsorbents an equal alternative with regard to absorbency and when compared to the superabsorbents which are commonly being used today. Moreover, there exists a need for a superabsorbent material for use in disposable absorbent articles and which is produced from cheap and readily available renewable starting materials.

SUMMARY OF THE INVENTION

The present invention provides a process for the production of superabsorbent materials of the kind mentioned in the introduction and which exhibit improved absorbency as compared to previously known superabsorbent materials of the same type.

The process according to the invention is primarily distinguished in that drying of a crosslinked liquid-swollen gel is carried out by extraction with a polar solvent.

A wide range of solvents may be used for the initial solution, containing the polysaccharide-based polymer starting material. However, the solution containing the starting material is preferably an aqueous solution.

Surprisingly, it has been shown that by drying a crosslinked polysaccharide with a polar solvent, such as ethanol, acetone or isopropanol, a superabsorbent material can be obtained exhibiting superior absorbency when compared to a material of the same composition but dried using another method. The improved absorbency is evident both in a higher absorption capacity and in a greater ability to retain absorbed liquid even when the absorption material is subjected to pressure. The absorbency of a superabsorbent material which has been dried with a polar solvent is considerably higher than that of a corresponding superabsorbent material which has been dried using any other method, regardless of whether the absorbed liquid is water or a salt solution such as urine.

When comparing electron scanning micrographs of crosslinked superabsorbent gels with the same composition but dried in different ways, it is clearly evident that the microstructure of the dried gels, or xero-gels, show significant differences depending on the method of desiccation. Accordingly, an air-dried gel exhibits a dense, compact structure while a gel which has been dried by solvent extraction exhibits a structure with a high degree of microporosity. Vacuum drying produces a structure exhibiting some degree of microporosity and can be said to represent a form between the structure obtained by air-drying and the structure obtained by the solvent drying in accordance with the invention.

A probable explanation of the advantageous effect of solvent drying, is that a commonly occurring phenomenon producing a dense, horny, non-absorbing structure, is avoided. This phenomenon is well known to the person skilled in the art, even though its exact mechanisms have not yet been fully understood. However, the effect is that the crosslinked gel exhibits reduced swelling capability and, thus, reduced absorption capacity. Accordingly, in comparison with conventionally dried gels, a gel which has been dried with a polar solvent exhibits a more open and flexible structure, something that affects the absorption process in a positive way.

The solvent-dried superabsorbent polymer exists in the form of a microporous gel. The superior absorption properties exhibited by the gel are believed to be the result of liquid partly being bound in the gel in a conventional manner and partly being absorbed in the microvoids in the gel. When the gel absorbs liquid, the gel swells, whereby the size of the microvoids increases and the absorption capacity of the gel is enhanced.

The starting material may comprise a polymer blend comprising an electrically charged polysaccharide-based polymer and an electrically uncharged polysaccharide-based polymer. The ratio between the charged polymer and the uncharged polymer is preferably between about 2:1 and about 4:1 and most preferably about 3:1.

A major advantage afforded by the invention is that carboxymethyl cellulose (CMC) can be used as a starting material for the production of a superabsorbent material having high absorption capacity and good liquid retention. The fact that CMC is produced from wood which is a renewable material source and, further, that it is readily available and comparatively low in cost, makes CMC particularly suitable for use in disposable absorbent articles. Moreover, with regard to biodegradability and compostability, CMC exhibits excellent characteristics.

However, it has been found to be less suitable to use CMC as sole starting material for the production of a superabsorbent material, since CMC tends to form intramolecular crosslinks instead of crosslinks between different molecules. An absorption material having particularly good properties may, however, be obtained with a starting material comprising a mixture of CMC in the form of its sodium salt (CMCNa) and hydroxyethyl cellulose (HEC). A suitable proportion between the amount of CMCNa and HEC has thereby been found to be between about 2:1 and about 4:1 and preferably about 3:1. At a lower concentration of HEC, the resulting cross-linked gel does not exhibit sufficient gel strength. High concentrations of HEC should be avoided since the swelling capacity and, accordingly, the absorption capacity will be insufficient if the HEC concentration is too high.

Alternatively, it is possible to use combinations of other charged and uncharged polysaccharides. Some further examples of suitable charged polysaccharides are carboxymethyl starch, oxidized starch and oxidized cellulose. Suitable uncharged polysaccharides include, but are not limited to: ethylhydroxyethyl cellulose (EHEC), hydroxypropyl cellulose (HPC) and hydroxypropyl starch (HPS).

It is further possible to use pectin as starting material.

The polysaccharides are preferably crosslinked with a crosslinking agent producing covalent crosslinks. Some examples of crosslinking agents of this kind are divinylsulphone (DVS), acetaldehyde, formaldehyde, glutaraldehyde, diglycidyl ether, diisocyanates, dimethyl urea, epichlorohydrin, oxalic acid, phosphoryl chloride, trimetaphosphate, trimethylomelamine, polyacrolein. Naturally, it is also possible to use ionic crosslinking or physical crosslinking such as hydrophobic/hydrophilic interactions.

BRIEF DESCRIPTION OF FIGURES

The invention will hereinbelow be described in greater detail, by way of example only, and with reference to the Figures shown in the attached drawings, wherein.

Figure 12:
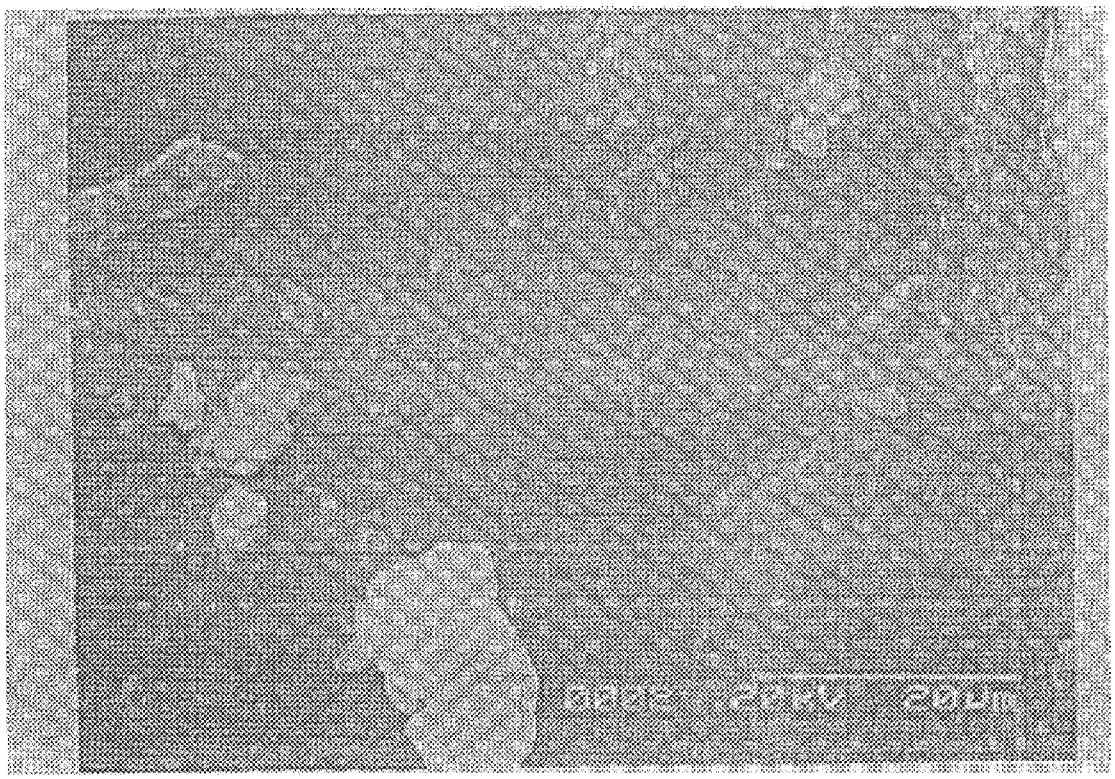
Figure 13:
Figure 14:
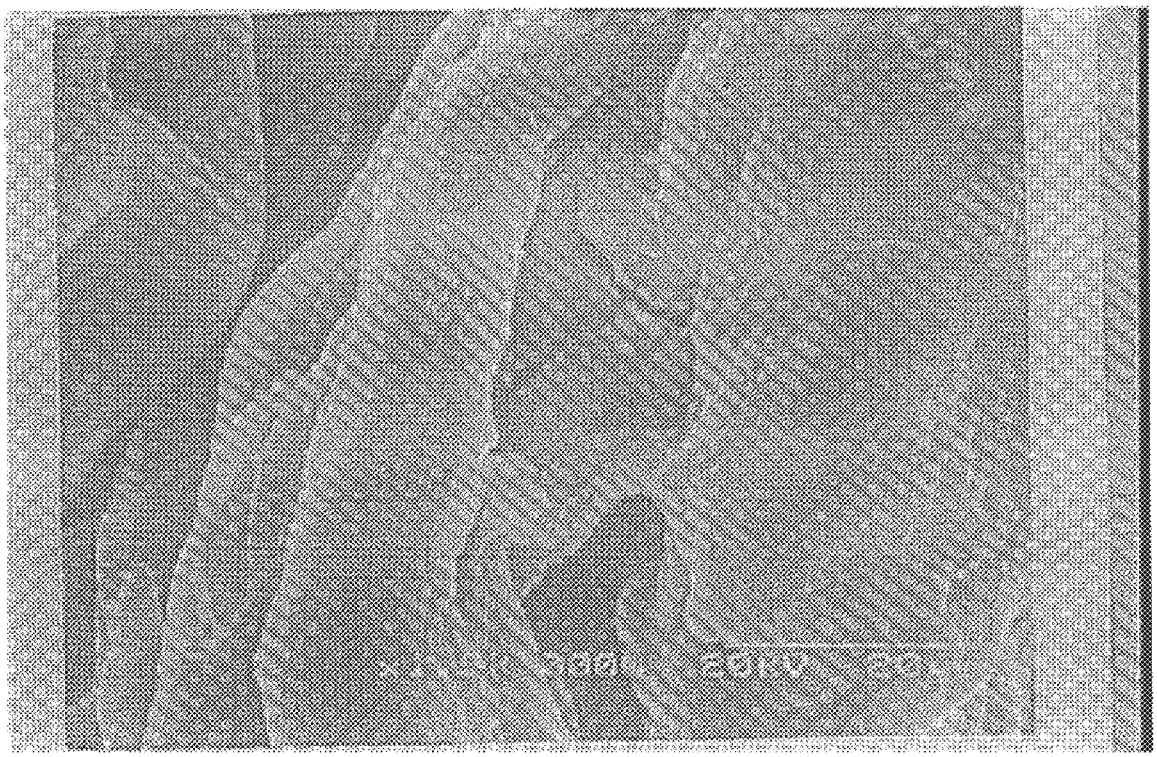

Additionally:

FIG. 12 shows an electron scanning micrograph of an air-dried gel;

FIG. 13 shows an electron scanning micrograph of a vacuum-dried gel;

FIG. 14 shows an electron scanning micrograph of a gel dried by extraction with acetone.

DETAILED DESCRIPTION OF METHODS

Preparation of Gel

The hydrogels which were used in the following examples were obtained by crosslinking mixtures of CMCNa and HEC, using DVS as crosslinking agent. The reason for choosing DVS as crosslinking agent is that DVS gives a reliable and reproducible crosslinking result. Thus, DVS is well suited for the production of crosslinked materials for use in comparative work. However, the invention shall not in any way be regarded as being restricted to the use of DVS as crosslinking agent. Accordingly, and as mentioned above, any suitable crosslinking agent or crosslinking method may be used.

The crosslinking reaction was performed in an alkaline aqueous solution with 0.02 M potassium hydroxide (KOH) at 20° C. CMCNa and HEC were dissolved in distilled water containing the desired amount of DVS. After thorough mixing for 24 hours, potassium hydroxide was added, thereby starting the crosslinking reaction. All reactions were performed with a reaction solution having an overall polymer concentration equal to 2% by weight.

After 24 hours, the crosslinked hydrogel was soaked in distilled water in order to reach equilibrium water sorption. The water surrounding the hydrogel was renewed at least three times. Each time, an amount of water corresponding to 5 times the weight of the hydrogel, measured immediately after the crosslinking reaction, was used. The soaking procedure was terminated after 36–48 hours. Subsequently, the swelled hydrogel was removed from the water and desiccated.

Desiccation Methods

Three different methods of desiccation were used:
i) air drying at atmospheric pressure
ii) drying under vacuum
iii) drying by extraction with a polar solvent Air drying consisted simply in leaving the swollen hydrogel at room conditions (25° C. and 50% relative humidity) until completely dry.

Vacuum drying was performed by placing swollen hydrogels in a container connected to a vacuum pump and kept at a pressure equal to 0.01 Torr.

Drying by extraction with a solvent consisted in placing water-swollen hydrogels in the solvent at room temperature and with gentle mixing. The solvent was replaced two times and the amount of solvent used each time was approximately twice that of the swollen hydrogel. The reason why acetone was used in all examples in which the gels were crosslinked with DVS is that, in contrast to the alcohols, acetone will not react with DVS. However, if crosslinking is carried out in an alternative manner, such as enzymatically, polar solvents such as ethanol or isopropanol may be used.

After desiccation, the dried gels produced by air drying and vacuum drying were ground in a laboratory grinder. In the solvent drying process, the stirring caused the gel to break into smaller pieces which were directly used in Examples 1–3. All subsequent measurements were performed on desiccated gel which had been ground or broken up into smaller pieces.

Free Swelling

Free swelling was determined using two different methods. Accordingly, in Examples 1–3, the ability of the gel to absorb liquid was measured according to a first method by immersing a piece of the gel in the test liquid and allowing the gel to absorb liquid until saturated. The gel was subsequently removed from the liquid and weighed.

In Example 4, the free swelling capacity on absorption was measured according to a second method by introducing 0.100 g +0.002 g crosslinked, dried gel in a test tube having the dimensions 150 mm×16 mm. The test tube was provided with a screw cap and had a volume of 20 ml. The height of the dry, unswollen sample was measured with a millimeter stick and was recorded. Thereafter, 15 ml synthetic urine was added with an automatic pipette.

The composition of the synthetic urine (SUR) was 60 mmol/l KCl, 130 mmol/l NaCl, 3.5 mmol/l $MgSO_4$, 2 mmol/l $CaSO_4.2H_2O$, 300 mmol/l urea, 1 g/l of a 0.1% solution of Triton X-100 which is a surfactant sold by Aldrich. The sample was left to swell for 2 hours until equilibrium was reached, whereafter the height was again measured and recorded.

From the thus obtained measurements, the change in volume/weight was calculated according to:

$$A(T) = \frac{(h(s) - h(t)) * \Pi * r^2}{m(t)}$$

A(T)=Absorption capacity in $cm^3/g$
h(s)=height in millimeters for the swollen sample
h(t)=height in millimeters for the dry sample
m(t)=the dry weight in grams for the sample
r=the radius of the test tube in millimeters (0,72 mm)

DESCRIPTION OF EXAMPLES

Example 1

The water uptake capability was measured according to the free swelling method, for different gels obtained by crosslinking an aqueous solution containing 2 percent by weight of a mixture of CMCNa and HEC, wherein the relation CMCNa:HEC=3:1, and with different amounts of crosslinking agent, divinylsulphone (DVS).

Figure 1:
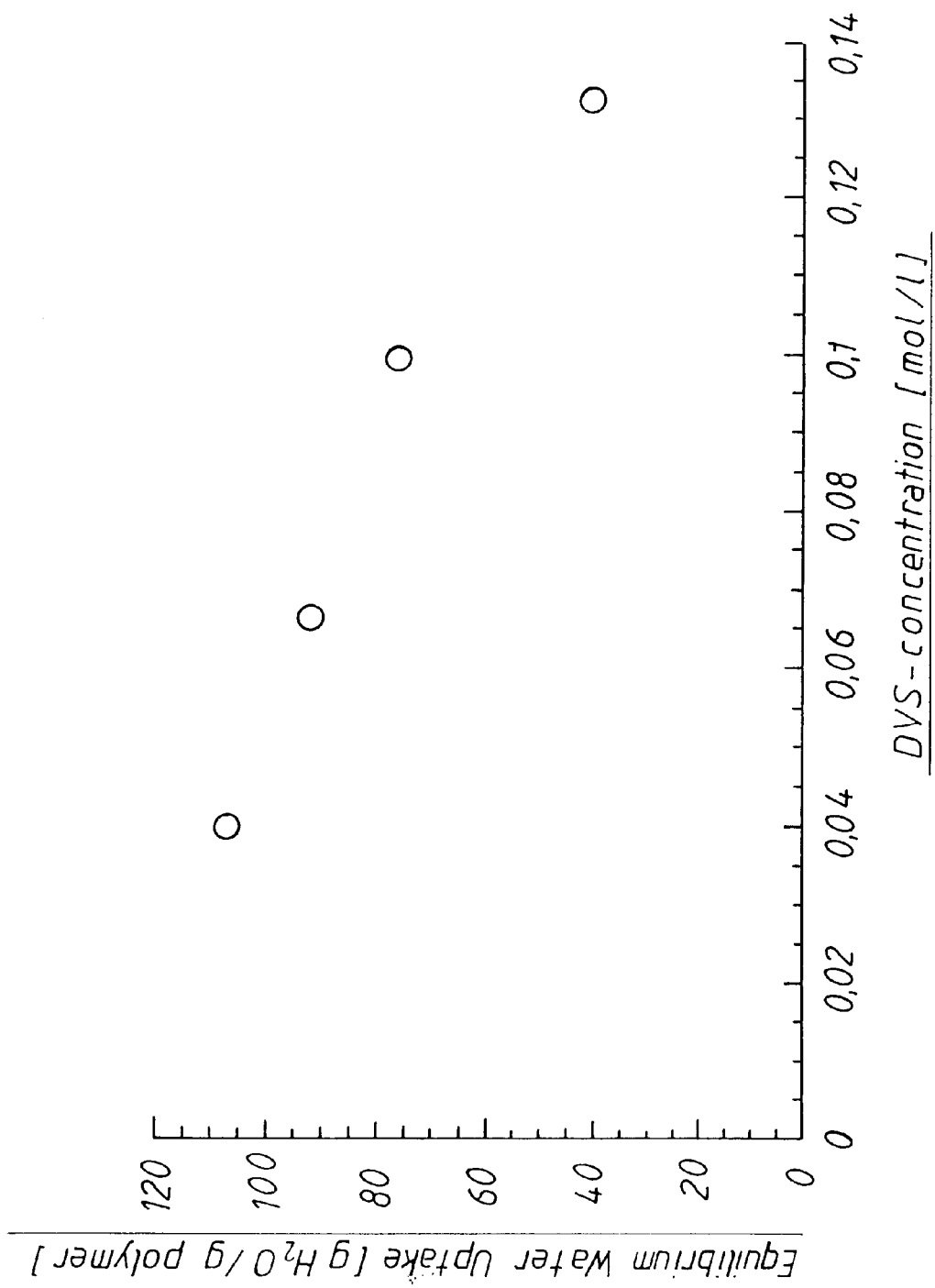
FIG. 1 shows the water uptake capability for air-dried gels produced with different amounts of DVS.

As can be seen in FIG. 1, the swelling capability for a gel-dried under room conditions (25° C., atmospheric pressure and 50% relative humidity) decreases with increasing content of DVS. The reason for this is that a higher degree of crosslinking increases the resistance to swelling of the gel. At a DVS-content below the lowest content of 0.04 mol/l given in FIG. 1, the gel strength of the resulting gel is not sufficiently high for the gel to be useful in practice.

Figure 2:
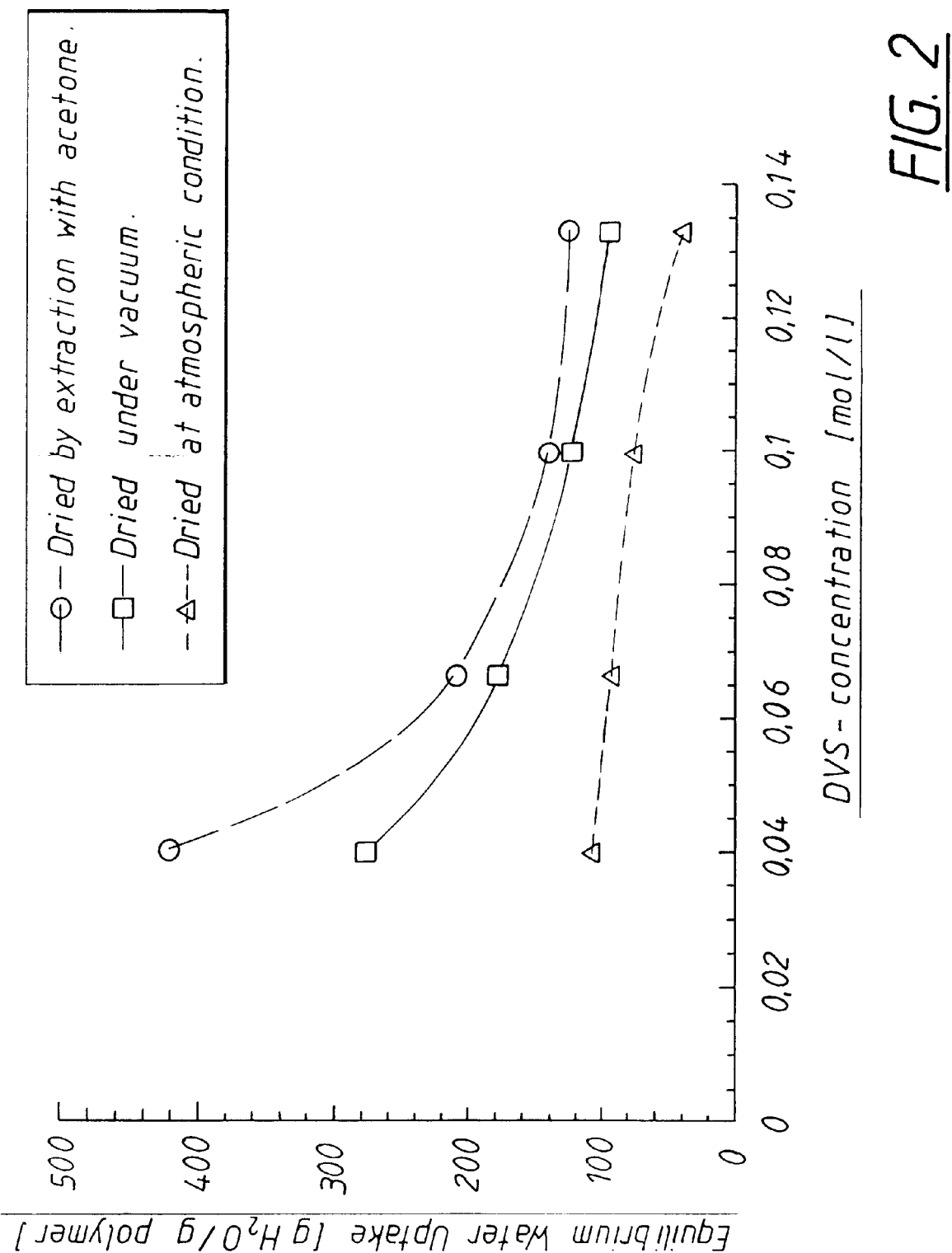
FIG. 2 shows the water uptake capability for gels dried using different methods and with different addition of DVS.

FIG. 2 illustrates how different desiccation methods affect the water uptake capability for the xero-gels presented in FIG. 1. As is clearly evident from FIG. 2, the gel which has been dried by extraction with acetone has a higher water uptake capability than corresponding air-dried and vacuum-dried gels. This statement is true regardless of the DVS-content.

Example 2

The water uptake capability was measured for different gels obtained by crosslinking and drying of a CMCNa/HEC-mixture in an aqueous solution containing 2 percent by weight of the CMCNa/HEC-mixture and with 0.04 mol/l DVS as crosslinking agent and further at different mixing ratios for CMCNa:HEC.

Figure 3:
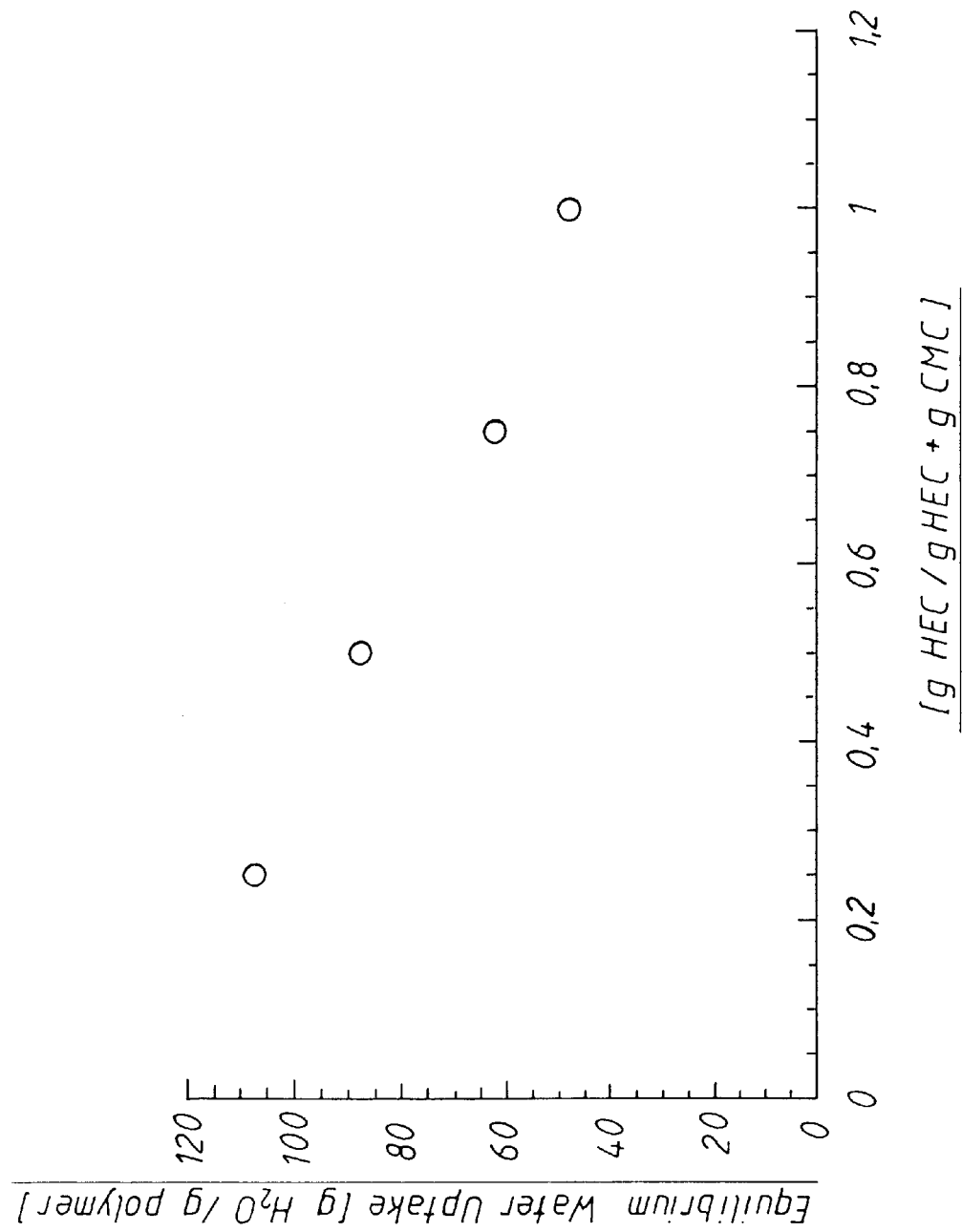
FIG. 3 shows the water uptake capability for air-dried gels with different concentration of HEC.

FIG. 3 shows how the water uptake capability for air-dried xero-gels decreases with increased content of HEC. The decrease in water uptake capability is partly due to the fact that the resistance to swelling of the gel is greater at a higher degree of crosslinking. By mixing CMCNa with HEC it is possible to increase the gel strength of the crosslinked gel, since HEC has a positive effect on the formation of intermolecular crosslinks. When the HEC content is below 0.25, the gel strength of the crosslinked gel is too low for most practical applications.

A further explanation of the reduction in liquid uptake capability with increasing HEC content may be that the amount of fixed ionic charges present on the macromolecular chains is decreased when the HEC content is increased.

Figure 4:
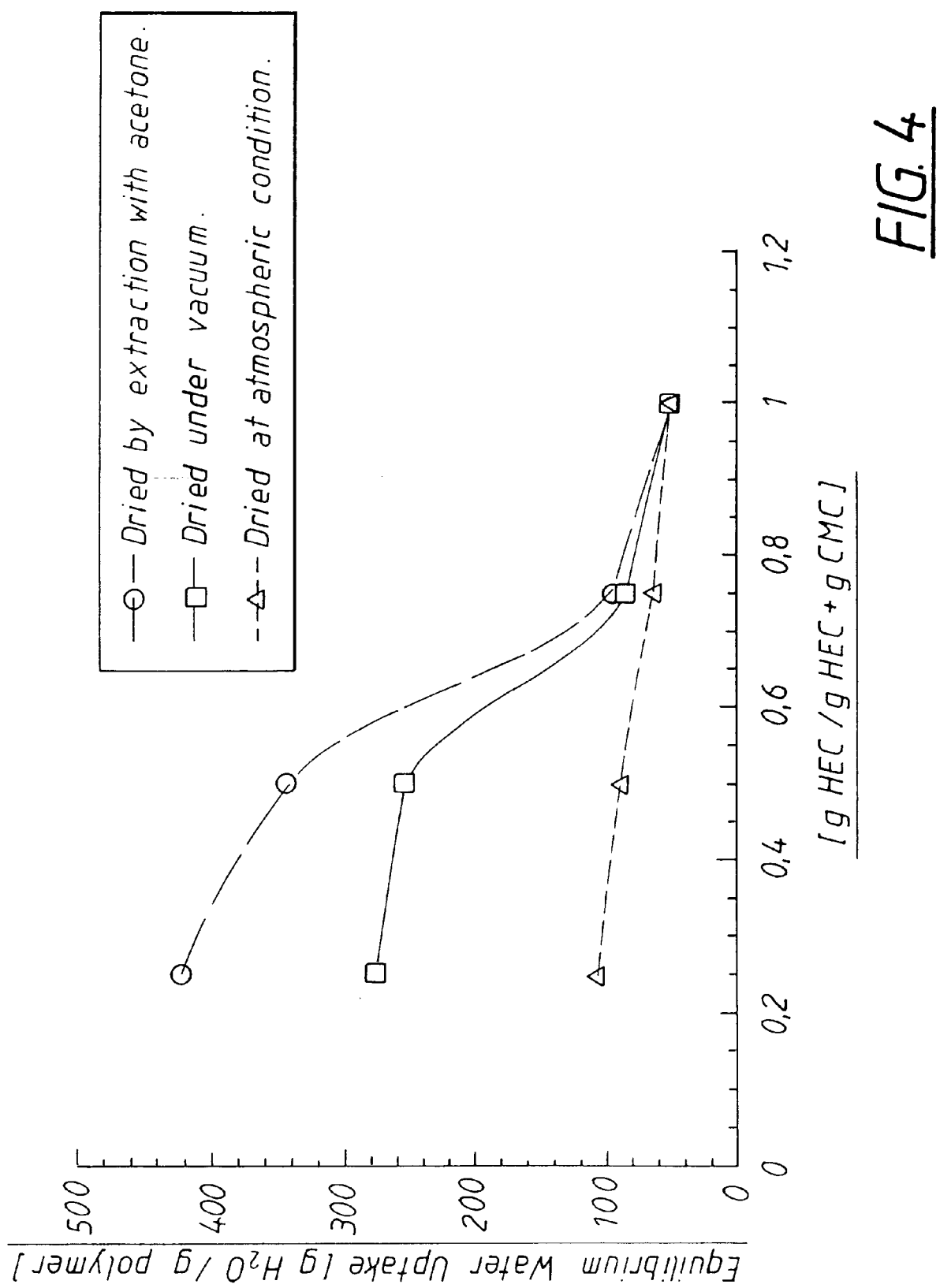
FIG. 4 shows the water uptake capability for gels dried using different methods and with different concentration of HEC.

The curves shown in FIG. 4 indicate that drying by extraction with acetone produces a significantly improved liquid uptake capability, as long as the HEC content does not exceed approximately 50% of the polymer mixture.

Example 3

The liquid uptake capability for hydrogels dried using different methods was compared when the absorbed liquid was a solution of NaCl in water. The ionic strength of the solution was 0.15 mol/l.

Figure 5:
FIG. 5 shows the liquid uptake capability in a solution of NaCl in water for gels dried using different methods and with-different DVS concentrations.

It is clear from FIG. 5 that acetone-dried hydrogel has a considerably higher uptake capability or swelling capacity than hydrogel which has been dried under vacuum or in air. The improved liquid uptake capability for acetone-dried hydrogel remains, as is evident from FIG. 5, even if the DVS concentration is changed.

Figure 6:
FIG. 6 shows the liquid uptake capability in a solution of NaCl in water for gels dried using different methods and with different relations in the mixture of CMCNa/HEC.

From FIG. 6, it can be deduced that acetone-dried hydrogel exhibits a higher liquid uptake capability in synthetic urine when compared to air-dried or vacuum-dried hydrogel, regardless of the ratio between the amount of CMCNa and the amount of HEC.

Figure 7:
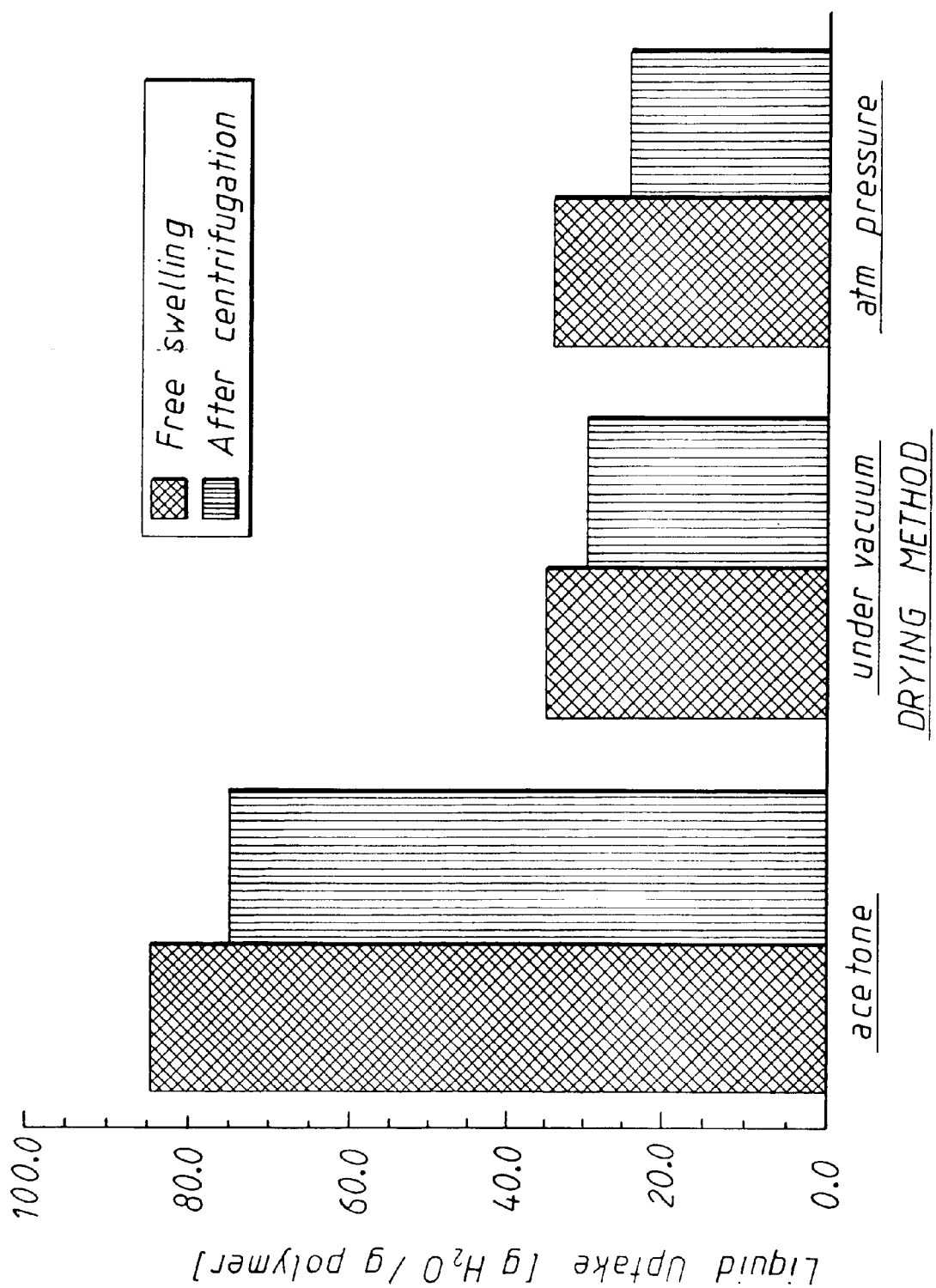
FIG. 7 shows the retention of synthetic urine for gels dried using different methods.
Figure 8:
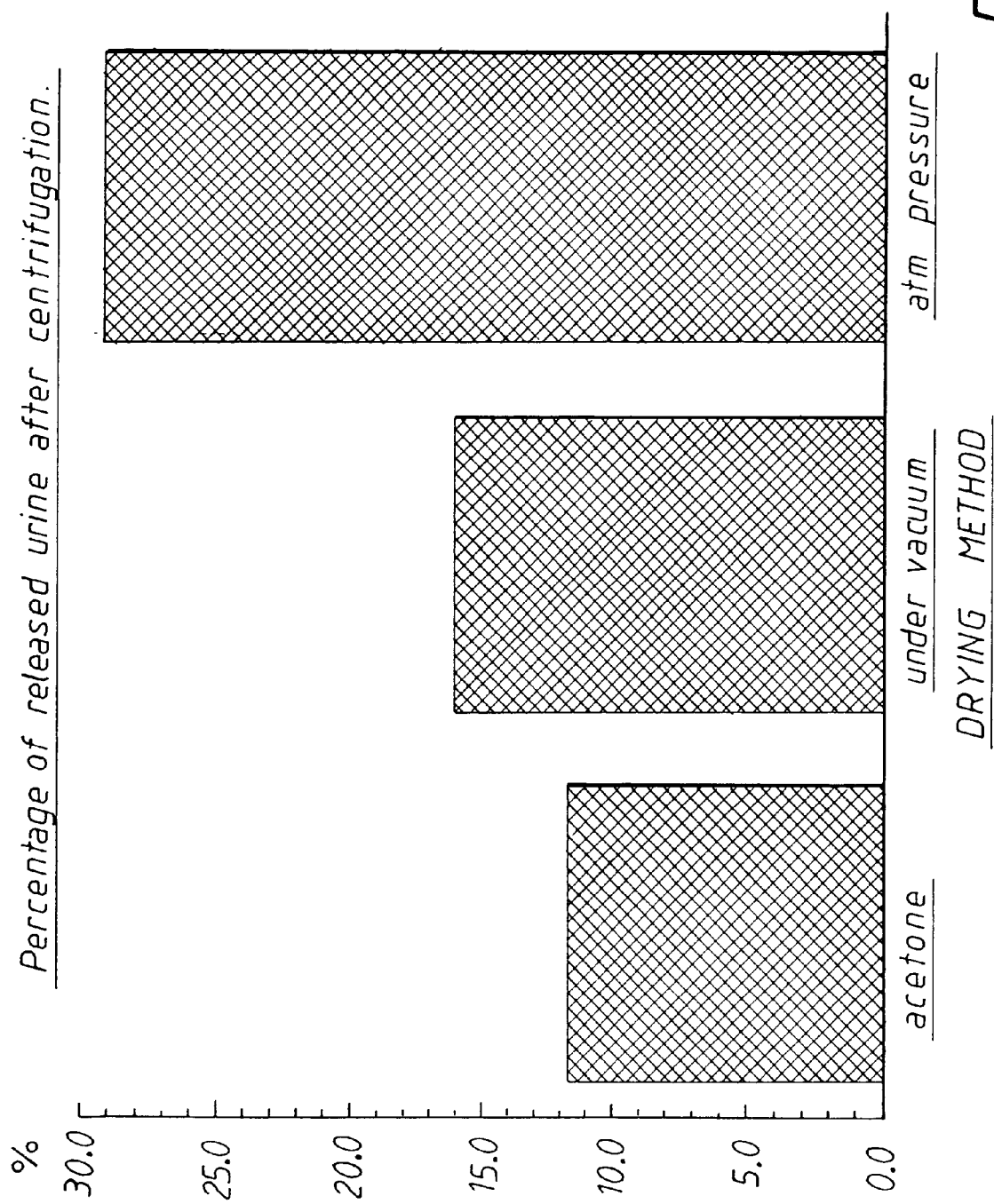
FIG. 8 shows the percentage of liquid which is released upon centrifugation of hydrogels dried using different methods.

In the tests presented in FIG. 7 and FIG. 8, synthetic urine (SUR) was used instead of the NaCl solution used in FIG. 5 and FIG. 6.

From FIG. 7, it is evident that the liquid retention capacity of acetone-dried hydrogel is higher than for gels which have been dried in other ways. Accordingly, the ability to retain liquid upon centrifugation of the hydrogels is higher for the acetone-dried gel than for hydrogels which have been dried in air or under vacuum, both in absolute numbers and in relation to the liquid uptake capability of the gels at free swelling.

In FIG. 8, it is shown that the portion of the synthetic urine which is extracted by centrifugation of a gel which has been allowed to swell freely in synthetic urine is smallest for acetone-dried gel and almost three times greater for air-dried gel.

Example 4

Figure 9:
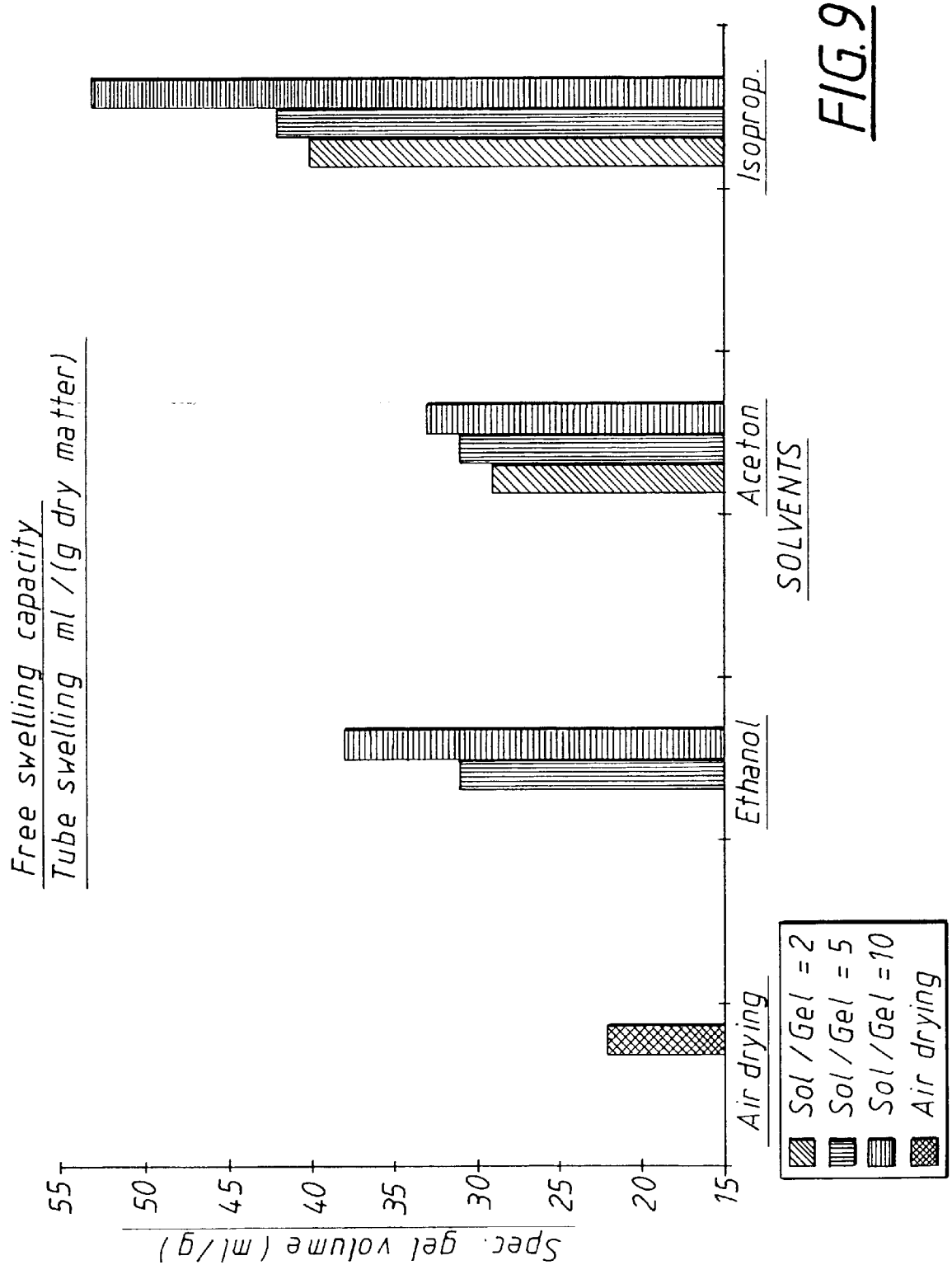
FIG. 9 shows the swelling capacity for a pectin-based absorption material after drying using different solvents.

In FIG. 9, it is shown how desiccation with different solvents affects the free swelling capacity of a crosslinked gel based on pectin, and how the relation in the mixture between the gel and the solvent affects the swelling capacity of the dried gel. The gel was crosslinked with an agent which could not react with alcohols, which means that when using solvents such as ethanol and isopropanol, no reaction between the alcohols and the crosslinking agent occured.

The swelling capacity for an air-dried, pectin-based gel is shown as a reference. The measurements were carried out by leaving the samples to swell freely in a test tube as described in the second of the free swelling methods.

As is apparent from FIG. 9, the swelling capacity for a gel which has been dried using isopropanol is better than for a gel which has been dried using ethanol or acetone. All solvent-dried gels exhibit a higher swelling capacity than an air-dried gel.

From the figure, it can further be seen that the relation between the amount of gel and the amount of solvent which is used in the drying process is important for the swelling capacity of the gel. Hence, the swelling capacity is higher for those gels in which a larger quantity of solvent was used, since, by using a larger quantity of solvent in the drying process, the water may be more fully extracted from the gel.

Example 5

In order to investigate how the polymer concentration in the starting reaction solution affects the final properties of the produced hydrogel, mixtures of CMCNa, HEC and DVS were prepared. The CMCNa:HEC ratio was 3:1 and the ratio (CMCNa+HEC): DVS was 4:1.

CMCNa, HEC and DVS were dissolved in distilled water at various polymer (CMCNa+HEC) concentrations, namely 3%, 2.5%, 2.3%, 2%, 1.7%, 1.5%, and 1%.

After crosslinking and desiccation in acetone, the dry polymer was immersed in distilled water until equilibrium was reached. The effect of the polymer concentration was assessed by measuring the swelling properties of the samples. The liquid swollen samples were weighed (using a Mettler AE 100 microbalance with an accuracy of $\pm 10^{-4}$ grams) and the results are found in FIG. 10. Accordingly, FIG. 10 shows the equilibrium swelling ratio in distilled water as a function of the polymer concentration of CMCNa+HEC in the starting reation solution.

Remarkable differences in water sorption capability were found among the investigated samples. However, the water uptake capability for the sample which was prepared from a 1% polymer solution could not be measured, since the gel strength of the resulting gel was insufficient.

Figure 10:
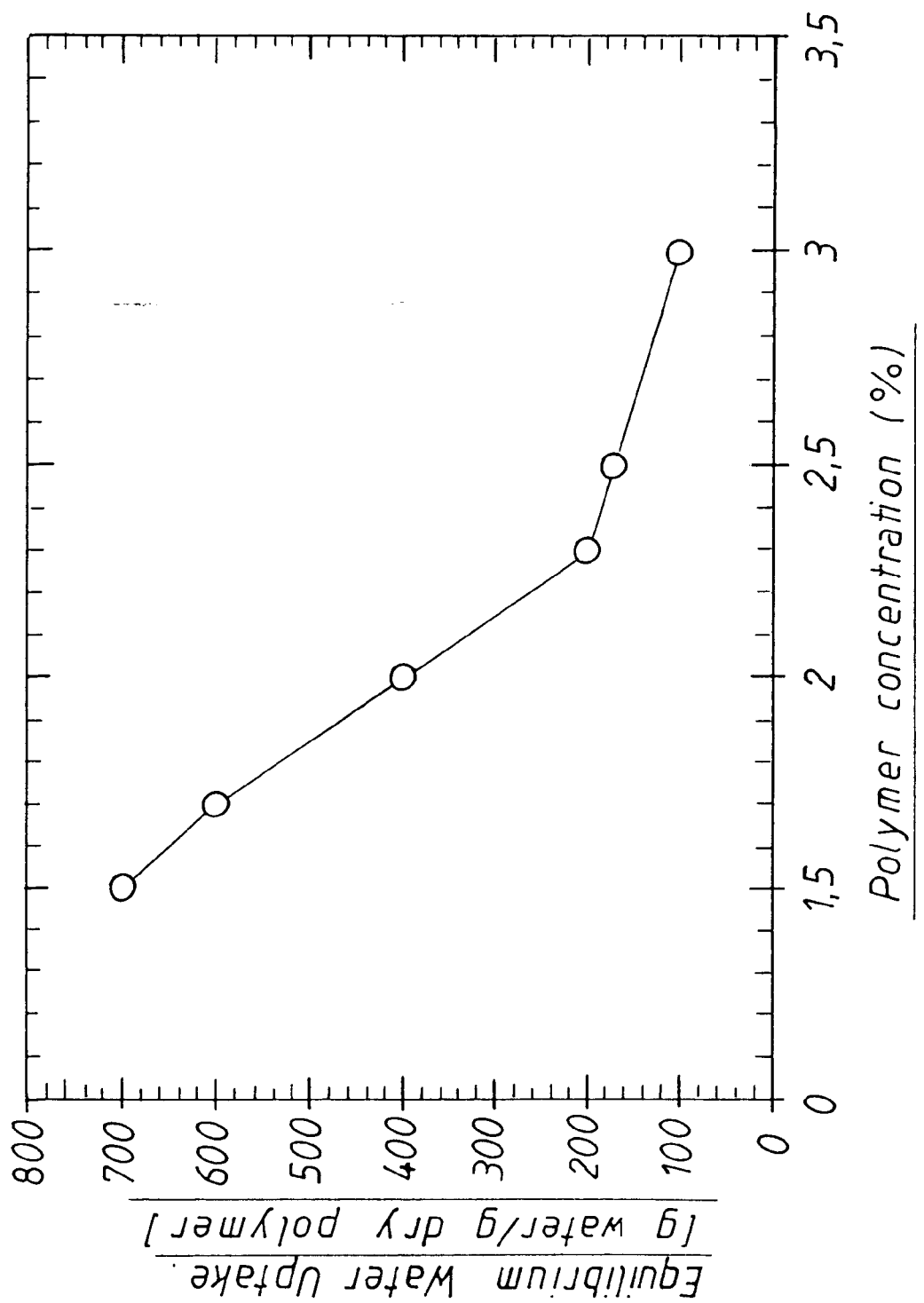
FIG. 10 shows the swelling ratio as a function of polymer concentration of CMC+HEC in the starting reaction solution.

As can be learned from FIG. 10, the equilibrium water content decreases as the polymer concentration in the starting solution increases. This effect is due to an increase in the network's elastic response to swelling. When the polymer concentration increases, the average molecular weight between two crosslinking points decreases. Accordingly, in order to obtain a gel having good absorption properties, the polymer concentration in the starting reaction solution should be between 1.5%–2.5%. The best compromise between mechanical properties and swelling capacity is obtained with a reaction solution having a polymer concentration of about 2%.

Example 6

In order to determine the effect on the water uptake capability of the ratio "weight of gel":"weight of acetone" during the dessication step, gels were prepared and dried in different amounts of acetone.

The gels had a CMCNa:HEC weight ratio of 3:1 and the DVS concentration was 0.04 mol/l. A water mixture containing 2% by weight of polymer (CMCNa+HEC) was prepared. Potassium hydroxide was used as a catalyst.

The polymer mixture was injected into spherical molds of different dimensions, where crosslinking took place. Subsequently, gel spheres were immersed in distilled water until equilibrium water absorption was reached. The hydrogel samples were desiccated using different gel/acetone weight ratios. The samples were finally completely desiccated in vacuum.

The desiccated spheres were then immersed in distilled water until equilibration. The swelling ratio was evaluated using an electronic microbalance (Mettler AE100) with an accuracy of ±104 grams.

Figure 11:
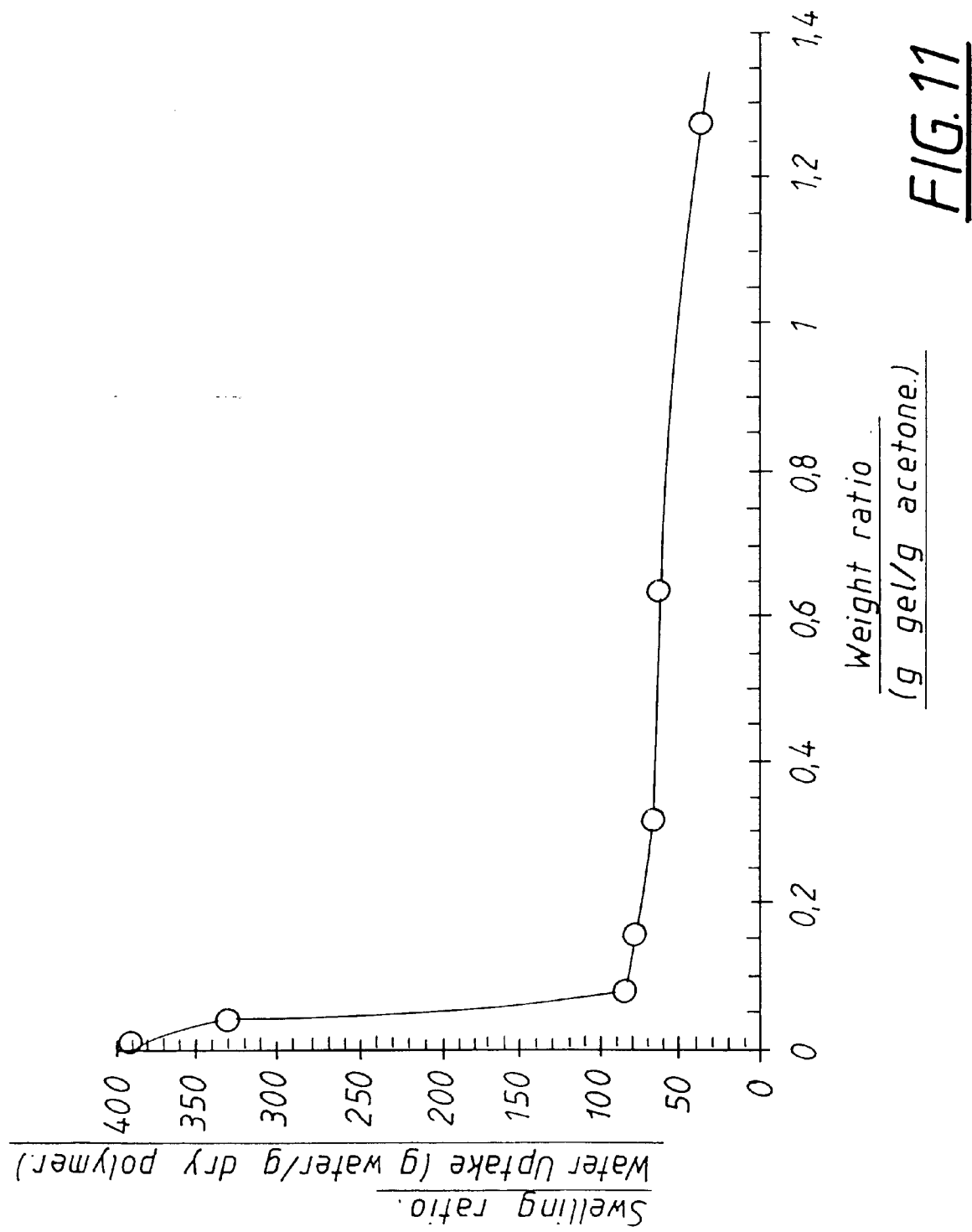
FIG. 11 shows the swelling ratio as a function of acetone concentration in the drying step.

The results of the measurements are found in Table 1 and in FIG. 11. The swelling capacity was found to increase dramatically if the ratio gel/acetone was decreased below approximately 0.06. Accordingly, the amount of acetone used per gram gel should be at least about 16.

TABLE 1

| swelling ratio (g of water/g of dry polymer) | weight ratio (g of gel/g of acetone) |
|---|---|
| 35.760 | 1.272 |
| 62.425 | 0.636 |
| 65.185 | 0.318 |
| 77.316 | 0.159 |
| 83.636 | 0.0795 |
| 329.76 | 0.0397 |
| 390.98 | 0.00636 |

DESCRIPTION OF FIGURES

As can be gleaned from the examples, the absorption capacity of the gels is highly dependent on the drying method which has been used. Thus, both the swelling capacity and the liquid uptake capability is lowest for air-dried gel, somewhat higher for gel which has been vacuum-dried and highest for gel which has been dried by extraction with acetone. These differences can probably be explained by the fact that different drying methods give the gels different morphological properties.

Accordingly, in FIGS. 12–14 there is shown the structure of a gel produced by crosslinking a 3:1-mixture of CMCNa and HEC and which has subsequently been dried in different ways. It is thereby evident from FIG. 12 that a gel which has been air-dried obtains a dense, compact bulk structure. The gel shown in FIG. 13 has a structure with a certain degree of microporosity, while the gel shown in FIG. 14 and which has been subjected to drying by extraction with acetone has a structure exhibiting a plurality of micropores.

The invention shall not be regarded as being restricted to the Examples described herein. Accordingly, several further embodiments are conceivable within the scope of protection of the appended claims.

What is claimed is:

1. A method for production of an absorbent polysaccharide-based absorption material, comprising:

crosslinking a liquid solution containing a starting material to produce an at least partially crosslinked liquid-swollen gel, wherein the starting material is a crosslinkable polysaccharide-based polymer blend comprising an electrically charged polysaccharide-based polymer and an electrically uncharged polysaccharide-based polymer; and drying the at least partially crosslinked gel by extraction with a polar solvent.

2. The method according to claim 1, wherein the solution containing the starting material is an aqueous solution.

3. The method according to claim 1, wherein the polar solvent is ethanol, acetone or isopropanol.

4. The method according to claim 3, wherein the polar solvent is acetone and the amount of acetone used per gram of at least partially crosslinked gel is at least 16.

5. The method according to claim 1, wherein crosslinking is carried out by adding a covalent crosslinking agent to the liquid solution.

6. The method according to claim 5, wherein the weight ratio between the charged polymer and the uncharged polymer is between 2:1 and 4:1.

7. The method according to claim 6, wherein the ratio between the charged polymer and the uncharged polymer is 3:1.

8. The method according to claim 1, wherein the starting material is a mixture of carboxymethyl cellulose and hydroxyethyl cellulose.

9. The method according to claim 1, wherein the liquid solution contains from 1.5% to 2.5% by weight of the crosslinkable polysaccharide-based polymer.

10. The method according to claim 9, wherein the liquid solution contains 2% by weight of the crosslinkable polysaccharide-based polymer.

11. The method according claim 1, wherein the starting material comprises pectin.

* * * * *